United States Patent [19]

Suberg

[11] Patent Number: 5,057,519
[45] Date of Patent: Oct. 15, 1991

[54] 5-HT$_3$ ANTAGONISTS: USE IN REDUCING OPIATE TOLERANCE

[75] Inventor: Stacy N. Suberg, Northbrook, Ill.

[73] Assignee: Bristol-Myers Squibb Company, New York, N.Y.

[21] Appl. No.: 536,379

[22] Filed: Jun. 11, 1990

[51] Int. Cl.$^5$ .............................................. A61K 31/44
[52] U.S. Cl. .................................................... 514/282
[58] Field of Search ......................................... 514/282

Primary Examiner—Stanley J. Friedman
Attorney, Agent, or Firm—Michelle A. Cepeda

[57] ABSTRACT

The use of 5-HT$_3$ antagonists and their pharmaceutically acceptable salts in reducing tolerance to opiates in particular morphine.

7 Claims, 3 Drawing Sheets

# 5-HT3 ANTAGONISTS: USE IN REDUCING OPITATE TOLERANCE

BACKGROUND OF THE INVENTION

The present invention relates to a method for delaying the onset of tolerance to opiates, and thereby inhibiting the development of tolerance to and dependence on opiates, without substantial alteration of their analgesic effects.

2. Description of the Prior Art

Opiates have been used for centuries to treat pain. The prototype of the analgesia-producing opiates is morphine. Morphine is a rapid and effective treatment for pain, but its long term use is limited due to negative side effects. Of these negative side effects tolerance and dependence are the hardest to counteract. Research in the areas of tolerance and addiction indicates that they are pharmacologically distinct components of opiate administration. These types of data suggest that tolerance, addiction/dependence and analgesia may be modulated by different neurochemical systems and/or different receptor subtypes.

5-Hydroxytryptamine, ("5-HT"), commonly known as serotonin, has been demonstrated to interact with the opiate system. Anatomically, fibers from the predominantly opiate periaquaductal gray region ("PAG") have been shown to connect with the serotonergic dorsal raphe region. In awake, behaving animals, 5-HT reuptake inhibitors are able to potentiate opiate analgesia. In humans, administration of tryptophan, the precursor of serotonin improves tolerance to the analgesia producing stimulation of the PAG.

Due to the advent of receptor binding techniques, several receptor subtypes for 5-HT have been identified. In particular, the 5-HT$_3$ receptor subtype has been localized on pain transmitting primary afferent fibers. We thus chose to determine if the 5-HT$_3$ receptor 1) modulates morphine analgesia and 2) modulates the onset of tolerance to morphine analgesia.

The 5-HT$_3$ antagonist utilized herein are known compounds, having been previously described. European Pat. Appl. No. 099789 A$_1$, for example, discloses a series of benzamides of which 4-amino-N-(1-azabicyclo[2.2.2]oct-3-yl)-5-chloro-2-methoxybenzamide (zacopride) is the most important as potent antiemetic. U.S. Pat. No. 4,820,715 to Monkovic et al, discloses the synthesis of 4-amino-N-(1-azabicyclo[2.2.2]oct-3-yl)-2-(butan-2-on-3-yl)oxy-5-chlorobenzamide, (BMY 33462), and 4-amino-2-(butan-2-on-3-yl)oxy-5-chloro-n-[2-(diethylamino)ethyl]benzamide (batanopride).

PCT/GB87/00826, to Glazo, published Feb. 26, 1987, discloses the potential use for 5-HT$_3$ antagonists in treatment or prevention of withdrawal syndrome. 5-HT$_3$ antagonists are under study for treatment of chemotherapy and drug-induced nausea and emesis. They are also being studied as antimigrane, anxiolytic, and antipsychotic agents. More recently, 5-HT$_3$ are being studied as cognition enhancers.

SUMMARY OF THE INVENTION

In accordance with this invention, it has been found that 5-HT$_3$ antagonists delay the onset of tolerance to opiates. By delaying the onset of tolerance to opiates, the 5-HT$_3$ antagonists of the present invention can thereby inhibit the development of tolerance to, and physical dependence on opiates.

Coadministration of a 5-HT$_3$ antagonist with morphine delays the onset of morphine tolerance in rats compared to rats receiving morphine alone. Due to the fact that the 5-HT$_3$ antagonist acts specifically at the 5-HT3 receptor, these data indicate that other compounds possessing this receptor profile may act similarly.

Thus, it is a principal object of the present invention to provide a method for significantly delaying the onset of opiate tolerance.

Another object of the present invention is to provide a method for the administration of a therapeutically effective amount of the 5-HT$_3$ antagonist or a pharmaceutically effective acid addition salt thereof.

Still another object of the present invention is to provide a method for administration of the 5-HT$_3$ antagonist without substantial alteration of the analgesic properties of the opiate.

DETAILED DESCRIPTION OF THE INVENTION

Figure 1:
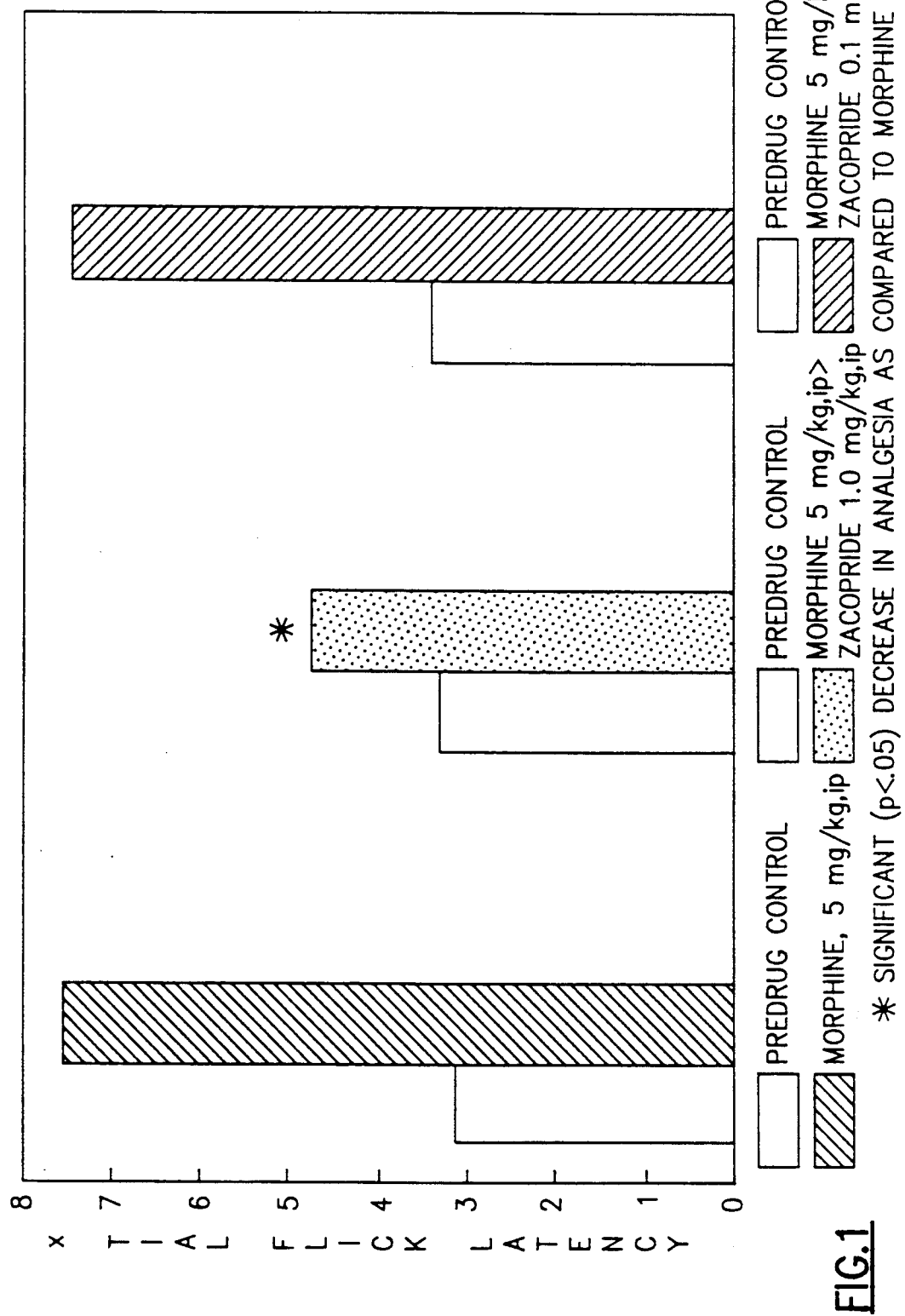
FIG. 1 shows the effect of zacopride on morphine analgesia

There appear to be three components of opiate administration: analgesia, tolerance and addiction. Recently, we have generated data that a subtype of the serotonin receptor, 5-HT$_3$, may modulate opiate tolerance. The data from these studies indicate that concomitant administration of a 5-HT$_3$ antagonist, preferably zacopride, batanopride or BMY 33462, with an opiate, preferably morphine, can delay the onset of tolerance to the analgesic effect of the opiate, and thereby inhibit the development of tolerance to and physical dependence on opiates. In addition, continuous administration of a 5-HT$_3$ antagonist can help to maintain responsiveness to further opiate administration. Further, due to the antiemetic properties of the 5-HT3 antagonist, coadministration of a 5-HT$_3$ antagonist with an opiate, would circumvent the nausea and vomiting caused by chemotherapy in cancer patients.

For the purpose of definition, the term tolerance as used herein is meant to mean a decreased response or sensitivity of the receptor to a repeated drug dose which requires increasing amounts to produce the same effect. Tolerance is usually manifested by a decreased duration of analgesia. Thus, the patient requires larger doses to produce the analgesic effects.

The tail flick test is a test used to detect agents capable of relieving moderate to severe pain, such as morphine and other narcotic analgesics. This procedure measures the time required for a rat to remove its tail from a radiant heat stimulus. The time at which the rat flicks its tail away from the heat source indicates its threshold for pain. Exposure time is limited to 8 seconds. The animals are tested prior to and after drug administration for their reaction time to the stimulus. A prolongation of the reaction time over predrug baseline is indicative of analgesia.

The tail flick test was used to observe the effect on morphine analgesia. In one study, zacopride at doses of 1.0 mg/kg, i.p. and 0.1 mg/kg, i.p., was administered concomitantly with 5 mg/kg, i.p. of morphine. It was found that 1.0 mg/kg, i.p. zacopride significantly attenuated morphine analgesia whereas the lower dose of 0.1 mg/kg, i.p. had no effect on morphine analgesia.

In another study, zacopride, when co-administered with morphine through minipumps for seven days, significantly delayed the onset of morphine tolerance. Furthermore, the animals which received both morphine and zacopride, though tolerant on day 7, regained analgesia upon challenge with a supramaximal dose of morphine. Animals implanted with morphine alone minipumps did not respond to the same supramaximal challenge dose of morphine.

The results from these studies indicate that the 5-HT$_3$ receptor may modulate serotonergic/opiate interactions and that 5-HT$_3$ antagonists may be useful in delaying the development of opiate tolerance. Due to the fact that the antagonist acts specifically on the 5-HT$_3$, receptor, these data imply that the 5-HT$_3$ antagonist may modulate opiate tolerance and suggests that other compounds possessing this receptor profile may work in a similar fashion. Such agents may be useful in the clinical maintenance of analgesia in the pain patient in that the use of 5-HT$_3$ antagonists may prolong effective management of pain.

The preferred embodiment of this invention is practiced by concomitant administration of an opiate, preferably morphine with a 5-HT$_3$ antagonist, preferably zacopride, batanopride or BMY 33462.

The 5-HT$_3$ antagonists may be administered in free base form, or in pharmaceutically acceptable salt form, e.g. suitable acid addition salts and quaternary ammonium salts. Such salts exhibit the same order of activity as the free bases. The present invention accordingly also provides a pharmaceutical composition comprising a free base form or an acid addition salt thereof or a quaternary ammonium salt thereof, in association with a pharmaceutically acceptable diluent or carrier. Such compositions may be formulated in conventional manner.

Administration of the 5-HT$_3$ receptor antagonist, may be by parenteral, oral, intranasal, or rectal routes. Parenteral administration comprises injection, e.g. intravenous or intramuscular injection, as well as any other parenteral route of administration.

The preferred dosage being from about 0.25 to about 250 mg/day, but actual amounts will vary according to the particular compound being used, the particular formulation and host being treated. Many factors that modify the action of the drug will be taken into account by those skilled in the art, e.g. age, body weight, sex, diet, time of administration, route of administration, rate of execution, condition of the host, drug combinations, and reaction sensitivities. Optimal dosages for a given set of conditions can be ascertained by those skilled in the art using conventional dosage determination tests in view of the experimental data provided.

In the administration of acceptable dosage forms, any one of a variety of preparations may be compounded, for example: capsules, tablets, pills, powders, solutions, etc. In addition to the active agent there may be present additional substances used in the manufacture of pharmaceutical preparations such as binders, fillers and other inert ingredients.

In accordance with the foregoing the present invention also provides a compound of the invention as hereinbefore defined for use as pharmaceutical, i.e. for use in treating opiate tolerance, which method comprises administering to said subject an effective amount of the 5-HT$_3$ receptor or a pharmaceutically acceptable acid addition salt or quaternary ammonium salt thereof.

While the invention has been described with respect to various specified examples and embodiments, it is to be understood that the invention is no limited thereto.

EXAMPLE I

General Methodology

Male, Sprague-Dawley rats (CRL:CD(SD)BR) were restrainer trained in Lexan ® restraining cylinders for 1 hour per day, for a minimum of 5 days prior to testing or implantation of minipumps. The animals were group housed on a 12 hour light/dark cycle and allowed free access to food and water.

EXAMPLE II

Effect of Zacopride on Morphine Analgesia

Protocol

Rats (321–444 g) were separated into three groups which received either morphine (5.0 mg/kg, i.p., n=10), morphine and 1.0 mg/kg zacopride (n=7), or morphine and 0.1 mg/kg zacopride (n=7). After all rats were baseline for their pre-drug responses to the tail flick test, they were injected with drug and retested 30 minutes later. The mean response of two tail flicks was used to determine significance (ANOVA).

Results

A dose of 5 mg/kg, i.p. morphine produced a high level of analgesia (% maximum possible effect (MPE)=89.7). The combination of 1.0 mg/kg zacopride and 5 mg/kg morphine, i.p. produced a statistically significant reduction in the level of analgesia as compared to morphine alone (49%, p<0.05). The lower dose of zacopride (0.1 mg/kg) in combination with morphine had no effect on the level of analgesia, (see Table 1 and FIG. 1).

TABLE 1

| Effect of Zacopride on Morphine Analgesia | | | |
|---|---|---|---|
| Drug | Dose | Baseline [Latency (sec)] | Test [Latency (sec)] |
| Morphine | 5 mg/kg, i.p. | 3.13 | 7.50* |
| Morphine + Zacopride | 5 mg/kg, i.p. 1.0 mg/kg, i.p. | 3.29 | 5.13** |
| Morphine + Zacopride | 5 mg/kg, i.p. 0.1 mg/kg, i.p. | 3.35 | 7.65 |

*p < .05 compared to baseline
**p < .05 compared to baseline and morphine alone

EXAMPLE III

Figure 2:
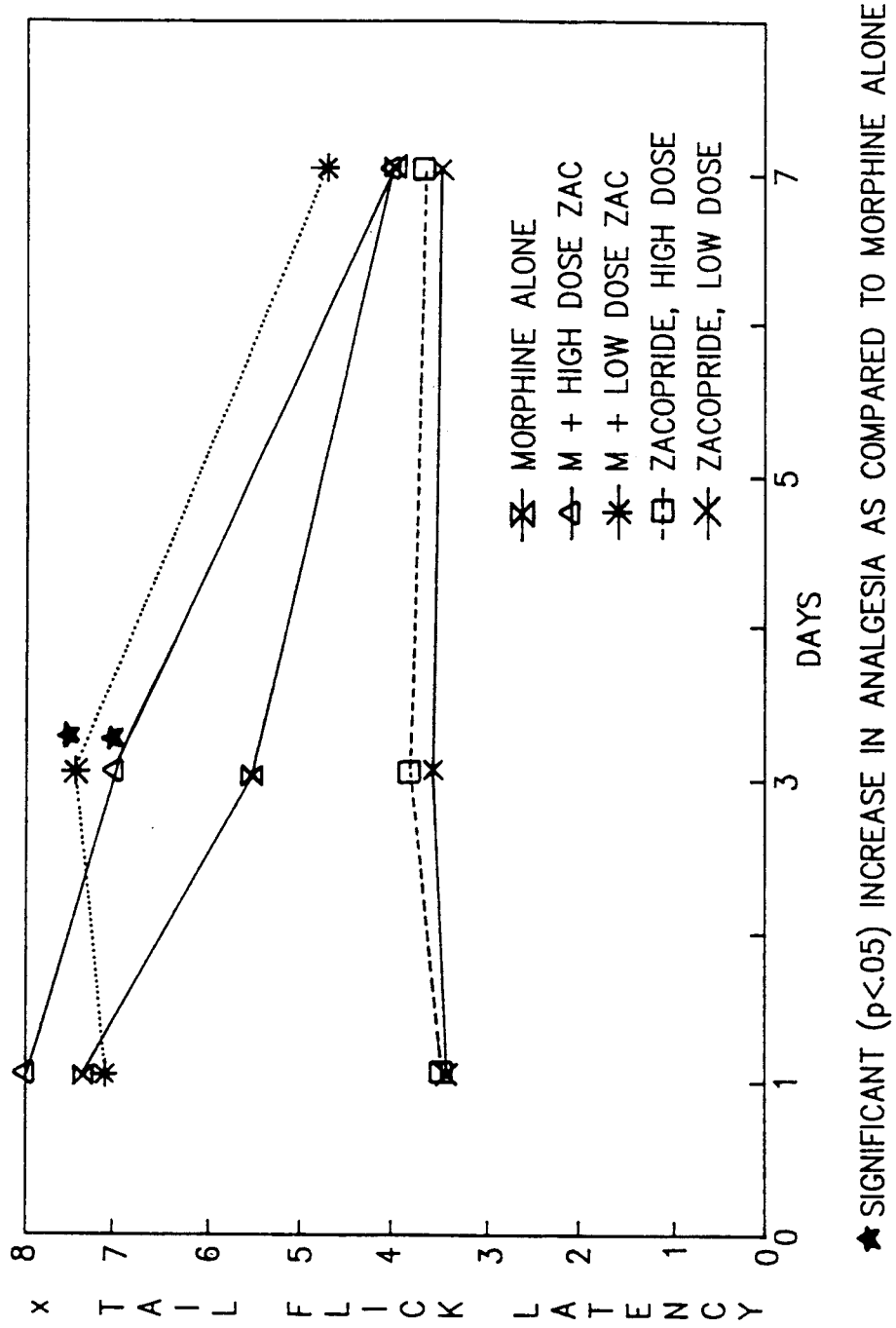
FIG. 2 shows the development of morphine tolerance

Effect of Zacopride on Morphine Tolerance (FIG. 2)

Seven minipumps (Alzet, 2 ML1, 12 µl/hr), were used in this study to provide a continuous s.c infusion of morphine. In a previous study, we had determined the rate of onset of morphine tolerance by administering 200 mg/7 days (12 µl/hr). Since we had determined in Study 1 (Example II) that a 1:5 ratio of zacopride to morphine resulted in significantly reduced analgesia and 1:50 ratio of zacopride to morphine had no effect, we chose similar dose ratios for the tolerance study: 40 mg and 4 mg of zacopride, respectively.

In total, there were five drug groups in this study: morphine alone (200 mg/7 days), n=9; zacopride alone (40 mg/7 days), n=9; zacopride alone (4 mg/7 days), n=9; morphine (200 mg/7 days)+zacopride (40 mg/7 days), n=10; and morphine (200 mg/7 days)+zacopride (4 mg/7 days), n=8. In the groups to receive a combination of morphine and zacopride, both drugs were placed into the same pump. Drugs were dissolved in 2 ml saline. The pumps were then implanted under methoxyflurane anesthesia.

The rats were tested for their response to the tail flick test at 24, 48, and 72 hours after implant. Two latencies were measured, and the mean response was calculated. On day 7 (168 hrs) immediately after tail flick latencies were recorded, all rats received an i.p. challenge injection of 10 mg/kg morphine, and the tail flick latencies were retested.

Results

Morphine Alone

Table 2 and FIG. 2 summarize the results with Zacopride on the development of morphine tolerance. On day 1 the rats had received 28.8 mg of morphine. Under these conditions, the mean tail flick latency was 7.40 sec (maximum response=8.0 sec), representing 86% of the maximum possible effect.

After 3 days the rats had received 86.4 mg of morphine. The mean response was significantly decreased ($p<.05$) to 5.58 sec (% MPE=46.8%). This indicates that tolerance occurred to the analgesic effect of continuous morphine.

On day 7, the rats had received 200 mg of morphine. The latency of their tail flick responses had dropped non-significantly from those at day 3 to 4.06 sec (% MPE=11.8).

Figure 3:
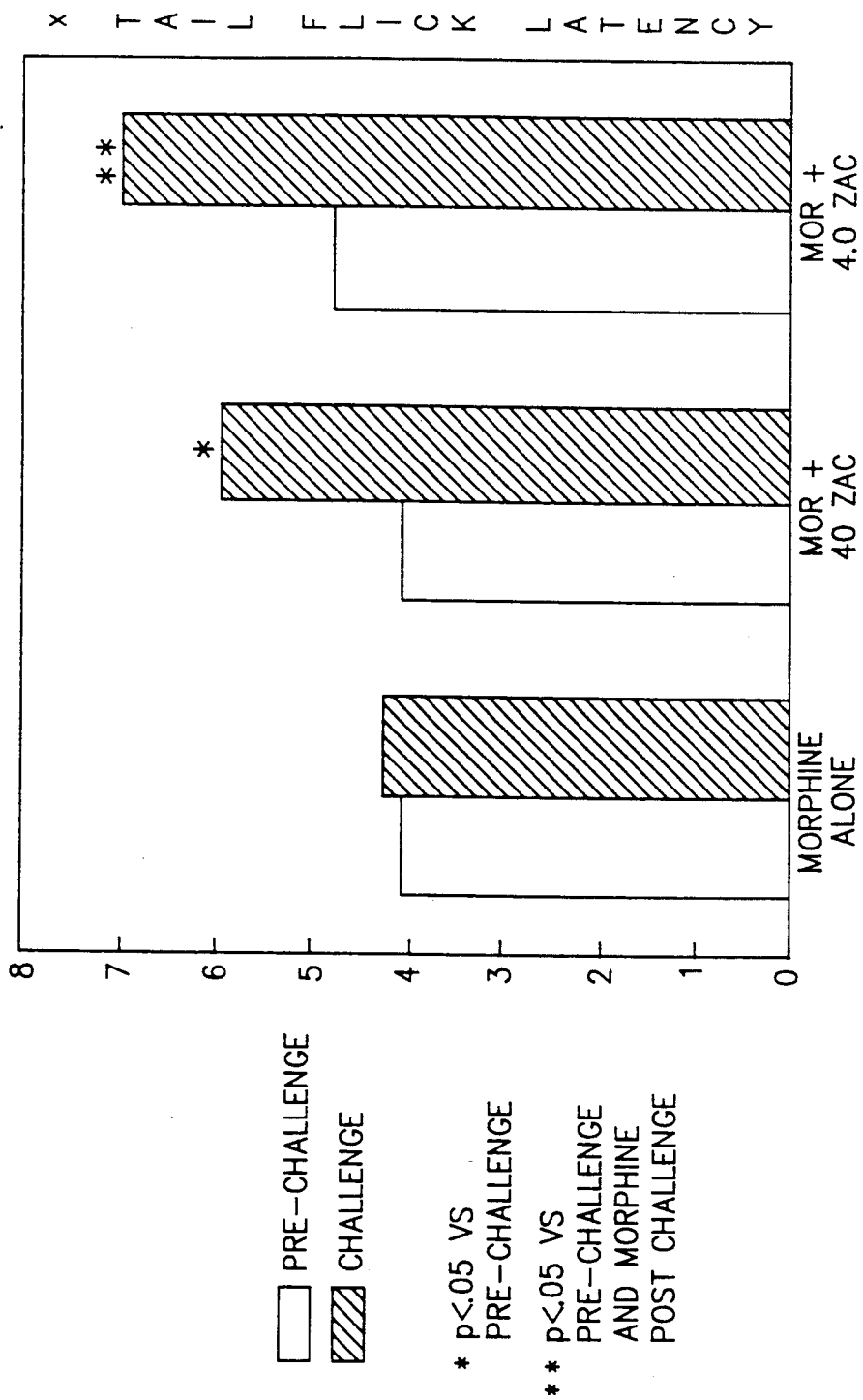
FIG. 3 shows the response to morphine challenge on day 7.

When the rats received a subsequent dose of morphine (10 mg/kg, i.p.) to test their responsiveness to a dose of the opiate which would produce a maximal analgesic response to tail flick in non-tolerant rats, there was no significant increase in tail flick latencies (4.06 sec pre-challenge vs 4.29 sec post-challenge), see Table 2 and FIG. 3.

Inability to demonstrate analgesia after administration of this supramaximal analgesic dose of morphine further confirmed that the animals were tolerant to morphine.

Zacopride Alone (40 mg dose)

Treatment with zacopride had no effect on tail flick latencies at any time during the study compared to predrug baseline latency. Administration of morphine on day 7 resulted in a maximal analgesic response, see Table 2.

Zacopride Alone (4 mg dose)

Treatment with zacopride had no effect on tail flick latencies at any time during the study compared to predrug baseline latency. Administration of morphine on day 7 resulted in a near maximal analgesic response, see Table 2.

Zacopride+Morphine (40 mg+200 mg)

On day 1 the cumulative dose of zacopride and morphine was 5.76 mg and 28.8 mg, respectively. The mean tail flick response was 8.00 sec, (% MPE=100%). This was not significantly different from the mean latencies of the morphine alone group.

On day 3, the rats had received 17.28 mg of zacopride and 86.4 mg of morphine. The mean tail flick latency was 7.05 sec. This dose produced a mean tail flick latency which was not significantly different from that for morphine alone on day 1, but was significantly greater than that for morphine alone on day 3. Thus, this combination of morphine and zacopride significantly prevented the onset of tolerance compared to the group of animals that received morphine alone.

On day 7, the rats had received 40 mg of zacopride and 200 mg of morphine. The mean tail flick latency was 4.04 sec. This value is not significantly different from that of morphine on day 7, indicating that tolerance had occurred. Upon administration of the challenge dose of morphine, tail flick latency increased to a mean of 5.93 sec, a value significantly greater than the pre challenge tail flick latency but not different from that of the group receiving morphine alone.

Zacopride+Morphine (4 mg+200 mg)

On day 1 the cumulative doses of zacopride and morphine were 0.576 mg and 28.8 mg, respectively. The mean tail flick response was 7.14 sec. This is not significantly different from the mean latency of the morphine alone group or the higher dose of zacopride (40 mg)+morphine group on day 1. The average weight of the rats was 437 g.

On day 3, the cumulative doses of zacopride and morphine were 1.728 mg and 86.4 mg, respectively. The mean tail flick response was 7.49 sec which was significantly greater than the latencies of the morphine alone group. There was no significant difference between the two zacopride+morphine groups. The average weight of the rats was 425 g.

The cumulative doses of zacopride and morphine reached 4 mg and 200 mg on day 7. As seen with the other combination group, the tail flick latencies decreased. A mean value of 4.78 sec was reached which was not significantly different from the morphine alone group. Upon receiving the challenge dose of morphine, the tail flick latencies increased significantly to 7.01 sec. The increase in analgesia was significant compared to the pre challenge tail flick latency and the post challenge tail flick latency in the morphine alone group, see Table 2.

TABLE 2

Effect of on Continuous Administration (7 days) of Zacopride (Zac) and Morphine (Mor) on tail-flick latency in response to supramaximal morphine

| Drug | Day 1 [Latency (sec)] | Day 3 [Latency (sec)] | Day 7 [Latency (sec)] | Post-Challenge Tail Flick [Latency (sec)] |
|---|---|---|---|---|
| Morphine | 7.40$^a$ | 5.58$^a$ | 4.06 | 4.28 |
| Zacopride | 3.55 | 3.88 | 3.71 | 8.00$^d$ |
| Zacopride | 3.49 | 3.64 | 3.55 | 7.23$^d$ |
| Mor + Zac$^e$ | 8.00$^a$ | 7.05$^b$ | 4.04 | 5.93$^c$ |
| Mor + Zac$^f$ | 7.14$^a$ | 7.49$^b$ | 4.78$^a$ | 7.01$^d$ |

$^a$significant compared to baseline
$^b$significant compared to morphine alone
$^c$significant compound to pre-challenge
$^d$significant compound to pre-challenge and morphine post-challenge
$^e$zacopride (40.0 mg dose)
$^f$zacopride (4.0 mg dose)

EXAMPLE IV

Effect of Batanopride and BMY 33462 on Morphine tolerance

Table 3 summarizes the results with batanopride and BMY 33462 on the development of morphine tolerance.

Batanopride significantly delayed the onset of opiate tolerance through day 5. Upon supramaximal challenge with morphine, tail flick latencies were significantly higher than morphine post-challenge but not from batanopride plus morphine pre-challenge.

BMY 33462 significantly delayed the onset of morphine tolerance when concomitantly administered with morphine in osmotic minipumps over 7 days. By day 5, BMY 33462 produced a significantly better delay in onset of morphine tolerance than batanopride. Even on day 7, BMY 33462 coadministered with morphine produced significantly higher tail flick latencies than morphine alone.

These data taken together with the significantly higher tail flick latencies with BMY 33462 and morphine on day 7 are consistent with data obtained in the Bezold-Jarisch reflex assay which indicate that BMY 33462 is a more potent 5-HT$_3$ antagonist than batanopride. Upon supramaximal morphine challenge, the animals were significantly more analgesic than those receiving morphine, indicating that BMY 33462 can maintain responsivity to further administration of the opiate. These results are similar to those seen with zacopride.

TABLE 3

Effect of BMY 33462 and Batanopride (Bat) on Continuous Administration of Morphine (Mor)

| Drug | Day 1 [Latency (sec)] | Day 3 [Latency (sec)] | Day 5 [Latency (sec)] | Day 7 [Latency (sec)] | Plus Morphine [Latency (sec)] |
|---|---|---|---|---|---|
| Saline | 3.54 | 4.01 | 3.67 | 3.55 | 7.74$^{d,e}$ |
| Batanopride | 4.01 | 4.09 | 3.70 | 3.52 | 6.96$^{d,e}$ |
| BMY 33462 | 3.78 | 4.52 | 3.70 | 3.93 | 7.75$^{d,e}$ |
| Morphine | 7.19$^a$ | 4.68 | 3.69 | 3.48 | 2.80 |
| Mor + Bat | 7.68 | 7.55$^{a,b}$ | 4.78$^{a,b}$ | 4.29 | 5.06$^e$ |
| Mor + BMY 33462 | 8.00$^a$ | 7.59$^{a,b}$ | 6.10$^{a,b,c}$ | 4.50$^{a,b}$ | 5.61$^{d,e}$ |

$^a$significant (p < 0.05) compared to saline.
$^b$significant (p < 0.05) compared to morphine.
$^c$significant (p < 0.05) compared to batanopride.
$^d$significant (p < 0.05) compared to pre-challenge.
$^e$significant (p < 0.05) compared to morphine post-challenge.

Because CNS studies on animals can in most cases be transferred to humans, the clinical implication of these results are clear. 5-HT$_3$ antagonists are beneficial in delaying the onset of morphine tolerance and maintaining responsivity to further administration of opiate.

Although this invention has been disclosed in detail with particular reference to certain preferred embodiments thereof, it is understood that variations and modifications can be effected within the spirit and scope of the appended claims. It is intended that all material contained in the above description, tables and figures shall be interpreted in an illustrative and not in a limiting sense.

What is claimed is:

1. A method for significantly delaying the onset of opiate tolerance, which method comprises concomitantly administering an opiate with a therapeutically effective amount of a benzamide-type 5-HT$_3$ antagonist, or a pharmaceutically effective acid addition salt thereof, to a patient in need of such treatment.

2. The method of claim 1 wherein the opiate is morphine.

3. The method of claim 1 wherein the benzamide-type 5-HT$_3$ antagonist is zacopride.

4. The method of claim 1 wherein the benzamide-type 5-HT$_3$ antagonist is batanopride.

5. The method of claim 1 wherein the benzamide-type 5-HT$_3$ antagonist is BMY 33462.

6. The method of claim 1 wherein the dosage is about 0.25 to about 250 mg/day.

7. The method of claim 1 wherein the amount of said benzamide-type 5-HT$_3$ antagonist is sufficient to inhibit the development of tolerance to and physical dependence on the opiate without substantial alteration of the analgesic properties of the opiate.

* * * * *